United States Patent [19]
Ogihara et al.

[11] Patent Number: 6,010,708
[45] Date of Patent: *Jan. 4, 2000

[54] COSMETICS AND N-ACYLAMINO ACID COMPOSITION

[75] Inventors: Kimihiko Ogihara; Hisashi Yamashita; Yoshihiro Takayama; Kazunori Ishigami, all of Ibaraki-ken, Japan

[73] Assignee: Kashima Oil Company, Tokyo, Japan

[ * ] Notice: This patent issued on a continued prosecution application filed under 37 CFR 1.53(d), and is subject to the twenty year patent term provisions of 35 U.S.C. 154(a)(2).

[21] Appl. No.: 08/956,397

[22] Filed: Oct. 23, 1997

[30] Foreign Application Priority Data

Oct. 29, 1996 [JP] Japan ................................. 8-286218

[51] Int. Cl.⁷ ........................................ A61K 7/00
[52] U.S. Cl. ................. 424/401; 424/70.1; 424/70.11; 424/195.1
[58] Field of Search .................. 424/401, 70.1, 424/70.11, 195.1

[56] References Cited

U.S. PATENT DOCUMENTS 5,540,853  7/1996  Trnh et al. ........................... 510/129

*Primary Examiner*—Thurman K. Page
*Assistant Examiner*—D. Faulkner
*Attorney, Agent, or Firm*—Oblon, Spivak, McClelland, Maier & Neustadt, P.C.

[57] ABSTRACT

There are disclosed cosmetics which comprise N-acylamino acids containing acyl groups having specifically numbered carbon atoms, or derivatives thereof and which are well suited for hair growth, skin care and the like; N-acylamino acid compositions which are favorably usable for detergents, dispersants, emulsifying agents, antimicrobial drugs, antiseptics, ultraviolet absorbers and the like. The invention provides cosmetics which comprise N-acylamino acids containing acyl groups having odd-numbered carbon atoms, salts thereof or esters thereof; N-acylamino acid compositions; and further N-acylamino acids containing acyl groups having carbon atoms in an odd number in the range of 13 to 17 along with salts and esters thereof.

11 Claims, No Drawings

COSMETICS AND N-ACYLAMINO ACID COMPOSITION

BACKGROUND OF THE INVENTION

1. Field of the Invention

The present invention relates to cosmetics, a N-acylamino acid composition, a novel N-acylamino acid and a derivative thereof. More particularly, it pertains to cosmetics which comprise a N-acylamino acid and/or a derivative thereof and which have excellent hair growth promoting effect, humectant action, subcutaneous blood flow rate increasing action and the like and thus are well suited for hair growth, skin care and the like; a N-acylamino acid composition which has excellent surface active action, disinfecting action, metal corrosion inhibiting action, etc. and thus is particularly useful as a detergent, dispersant, emulsifying agent, antimicrobial drug, antiseptics, ultraviolet absorber and the like; a N-acylamino acid, a salt thereof and an ester thereof being favorably used in the aforesaid purpose of use.

2. Description of the Related Arts

Cosmetics blended with various effective drugs have heretofore been known. For example, a hair growth agent is incorporated with, as effective drugs, a vitamin such as vitamin E; a vasodilator such as acetylcholine derivatives; an antiflammatory agent such as lithospermum root extract; female sex hormone such as elastodiol; a skin function enhancing agent such as cepharanthine; a melanin synthesis catalyst such as copper pantothenate; a keratolytics such as salicylic acid; and the like, said hair growth agent being used for the prevention and therapy of alopecia.

As an example in which a fatty acid or a derivative thereof is blended in cosmetics such as a hair growth agent, an example is known in which a natural vegetable oil such as olive oil or castor oil or stearic acid is blended for the purpose of improving the physical properties of a product. It is known that almost all of fatty acids which constitute various lipids of natural origin such as vegetable oils and animal oils is a fatty acid having even-numbered carbon atoms chain, whether the fatty acid is a saturated one such as stearic acid, palmitic acid, etc, or an unsaturated fatty acid such as oleic acid, linolenic acid, etc.

On the other hand, examples in which a fatty acid having odd-numbered carbon atoms or a derivative thereof is incorporated in hair cosmetics include the compound described in Japanese Patent Publication No. 41363/1988.

However, although it is said that the above-mentioned conventional cosmetics such as the hair growth agent are effective for the prevention and improvement of dandruff, itch, hair falling out and the like and besides promote hair generation and restoring, the real situation at the present time is that cosmetics which exert satisfactory effect have never been realized.

As a typical amino acid-based surfactant, there is known a group of N-acylamino acids that are obtained by the condensation reaction of amino acids and fatty acids. The aforesaid N-acylamino acids are imparted with a variety of functions such as high safety for environment and ecology, affinity for skin and hair, special association formation originating from the amide groups, chelate function and antioxidizing function, whereby they are expected to find a wide variety of application by making use of such characteristics.

There have heretofore been reported, as such N-acylamino acids, N-acylamino acids that are obtained by the condensation reaction of natural fatty acids and amino acids. As mentioned hereinbefore, almost all of the natural fatty acids, that is, the fatty acids which constitute various lipids of natural origin such as vegetable oils and animal oils is a fatty acid having even-numbered carbon atoms.

On the other hand, examples in which a derivative of a fatty acid having even-numbered carbon atoms such as a N-acylamino acid salt is blended in a detergent include the compound described in Japanese Patent Application Laid-Open No. 42809/1972.

However, the compositions comprising the above-mentioned conventional N-acylamino acid, although proposed to be applied to various uses such as a detergent, are still insufficient in surface active action, etc. thereby bringing about the actual circumstance at the present time that a composition which exhibits satisfactory effect has not yet been obtained.

SUMMARY OF THE INVENTION

Under such circumstances, it is a first object of the invention to provide cosmetics that are excellent in hair growth promoting effect, humectant action, subcutaneous blood flow rate increasing action and the like, thus well suited to use for hair growth, skin care, etc.

It is a second object of the invention to provide a N-acylamino acid composition which is excellent in surface active action, disinfecting action, metal corrosion inhibiting action, etc. and thus is particularly useful as a detergent, dispersant, emulsifying agent, antimicrobial drug, antiseptics, ultraviolet absorber and the like.

In addition, it is a third object of the invention to provide a novel N-acylamino acid and a derivative thereof that are favorably usable for the above-mentioned purposes of uses.

As a result of intensive research and investigation accumulated by the present inventors in order to attain the foregoing objects, it has been found that the first object is achieved by employing, as an effective component, N-acylamino acids containing acyl groups having odd-numbered carbon atoms (hereinafter sometimes referred to as "specific N-acylamino acid"), salts thereof or esters thereof in cosmetics in question; that the second object is achieved by a compositon which comprises N-acylamino acid containing acyl groups having odd-numbered carbon atoms, salts thereof or esters thereof; and besides that the third object is achieved by N-acylamino acid containing acyl groups having carbon atoms in an odd number within a specific range, salts thereof or esters thereof.

The present invention has been accomplished by the above-mentioned finding and information.

Specifically, the present invention provides:

(1) cosmetics which comprise, as an effective component, at least one member selected from the group consisting of N-acylamino acids containing acyl groups having odd-numbered carbon atoms and salts thereof (hereinafter referred to as "Cosmetics I");

(2) cosmetics which comprise, as an effective component, an ester of N-acylamino acids containing acyl groups having odd-numbered carbon atoms (hereinafter referred to as "Cosmetics II");

(3) a N-acylamino acid composition which comprises at least one member selected from the group consisting of N-acylamino acid containing acyl groups having odd-numbered carbon atoms, salts thereof and esters thereof;

(4) a N-acylamino acid containing an acyl group having carbon atoms in an odd number in the range of 7 to 19 or salts thereof; and (5) an ester of N-acylamino acid containing acyl groups having carbon atoms in an odd number in the range of 13 to 17.

DESCRIPTION OF THE PREFERRED EMBODIMENTS

First of all, description will be given of the cosmetics according to the present invention.

The Cosmetics I of the present invention comprises, as an effective component, at least one member selected from the group consisting of N-acylamino acid containing acyl groups having odd-numbered carbon atoms and salts thereof. The N-acylamino acid containing acyl groups having odd-numbered carbon atoms as used here and hereinafter means the N-acylamino acid in which at least one of amino groups in the amino acid has been acylated with acyl groups having odd-numbered carbon atoms.

As the amino acid to be used for the production of the above-mentioned N-acylamino acid containing acyl groups having odd-numbered carbon atoms and salts thereof, amino acids such as an amino acid of natural origin, a non-proteinic amino acid and an amino acid produced by chemical synthesis can be used and are exemplified by an a-amino acid, β-amino acid, γ-amino acid, δ-amino acid, aliphatic amino acid, aromatic amino acid, heterocyclic amino acid, neutral amino acid, basic amino acid and acidic amino acid. There are also usable amino acids having optical isomerism such as L-, D- and racemic isomers. Specific examples of the above-mentioned amino acids include alanine, valine, leucine, isoleucine, methionine, tryptophan, phenylalanine, glycine, serine, threonine, cysteine, tyrosine, asparagine, glutamine, lysine, arginine, aspartic acid, glutamic acid, β-alanine, hydroxylysine, ornithine, citrulline, 5-aminolevulinic acid and γ-aminobutyric acid.

With regard to the Cosmetics I of the invention, the compound represented by the general formula (I) is preferably used as a N-acylamino acid contianing an acyl group having odd-numbered carbon atoms,

(I)

wherein R is a straight chain aliphatic hydrocarbon group having even-numbered carbon atoms which may have substituent group; $R^1$ and $R^2$ are each a hydrogen atom, an alkyl group, a hydroxyalkyl group, an aryl group, a hydroxyaryl group, $-(CH_2)_y COOH$ or $-(CH_2)_z NH_2$, said groups may be substituted by a carboxyl group (—COOH) or an amino group (—$NH_2$); and x, y and z are each an integer from 0 to 4.

The straight chain aliphatic hydrocarbon group having even-numbered carbon atoms represented by R in the foregoing general formula (I), which may be saturated or unsaturated, is preferably exemplified by the group $CH_3(CH_2)_n-$ wherein n is an odd integer from 9 to 17.

In the Cosmetic I of the invention, the compound represented by the general formula (II) is preferably usable as the N-acylamino acid represented by the foregoing general formula (I)

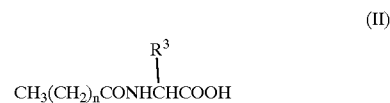

(II)

wherein $R^3$ is $-(CH_2)_y COOH$ in which y and n are each as previously defined in the general formula (I).

In the present invention, a compound in which y is 1 or 2 is preferably used. As the acyl group having odd-numbered carbon atoms in the N-acylamino acid containing acyl groups having odd-numbered carbon atoms, there is preferably usable an acyl group having carbon atoms in an odd number in the range of 11 to 19, preferably 13 to 17. In the case where the number of carbon atoms departs from the aforesaid range, the effect of the present invnetion is sometimes not sufficiently achieved. In addition, the N-acylamino acid is preferably derived from an acidic amino acid, especially from N-acylaspartic acid or N-acylglutamic acid.

Examples of the salt of the N-acylamino acid containing acyl groups having odd-numbered carbon atoms include an alkali metal salt derived from sodium or potassium, an alkaline earth metal salt derived from calcium, etc. and an ethanolamine such as monoethanolamine, diethanolamine and triethanolamine. Of these, a mono-salt, especially a monosodium salt and mono/triethanolamines are preferably used.

The amount of the N-acylamino acid containing acyl groups having odd-numbered carbon atoms or salts thereof to be blended in the Cosmetic I of the present invention can be suitably determined in accordance with the purpose of use, the mode of formulation, etc., and is usually selected in the range of 0.01 to 10% by weight based on the whole weight of the composition. The amount thereof to be blended therein, when less than 0.01% by weight, sometimes leads to failure to exert the effect of the present invention. On the contrary the amount thereof, when more than 10% by weight, is not favorable from the viewpoint of economical efficiency since the working effect approaches the uppermost limit.

The Cosmetics II according to the present invention comprises, as an effective component, an ester of the N-acylamino acid containing acyl groups having odd-numbered carbon atoms. The above-mentioned ester is an esterified product formed by the reaction of a N-acylamino acid in which at least one of amino groups in the amino acid has been acylated with an acyl group having odd-numbered carbon atoms and an alcoholic compound.

Examples of usable amino acids in the production of the aforestated N-acylamino acid containing an acyl group having odd-numbered carbon atoms, as is the case with the Cosmetics I, include an amino acid of natural origin, a non-proteinic amino acid and an amino acid produced by chemical synthesis, for example, an α-amino acid, β-amino acid, γ-amino acid, δ-amino acid, aliphatic amino acid, aromatic amino acid, heterocyclic amino acid, neutral amino acid, basic amino acid and acidic amino acid. There are also usable amino acids having optical isomerism such as L-, D- and racemic isomers. Specific examples of the above-mentioned amino acids are as previously exemplified in the aforesaid description of the Cosmetics I.

As the aforesaid N-acylamino acid which is a starting material for the N-acylamino acid ester in the Cosmetic II of the present invention, for example, the compound represented by the general formula (I) is used. The saturated or unsaturated straight chain aliphatic hydrocarbon group having even-numbered carbon atoms which is represented by R is preferably the group represented by $CH_3(CH_2)_m-$, wherein m is an odd integer from 5 to 17.

With regard to the Cosmetics II of the invention, the compound represented by the genreal formula (III) is preferably used as N-acylamino acids containing acyl groups having odd-numbered carbon atoms.

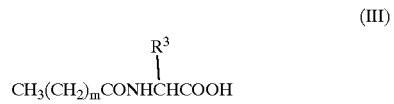

(III)

Wherein $R^3$ is $-(CH_2)_y COOH$ in which y is as previously defined in the general formula (I) and m is as just defined.

In the Cosmetics II of the present invention, a compound in which y is 1 or 2 is preferably used. As the acyl group having odd-numbered carbon atoms in the N-acylamino acid containing an acyl group having odd-numbered carbon atoms, there is usable an acyl group having carbon atoms in an odd number in the range of 7 to 19, preferably 11 to 19, more preferably 13 to 17. In the case where the number of carbon atoms departs from the aforesaid range, the effect of the present invention is sometimes not sufficiently achieved. In addition, the above-mentioned N-acylamino acid may be derived for use from any of an acidic amino acid, neutral amino acid and basic amino acid, and is preferably derived from an acidic amino acid, especially from N-acylaspartic acid or N-acylglutamic acid.

The alcoholic compound which forms an ester of the N-acylamino acid containing acyl groups having odd-numbered carbon atoms in the Cosmetics II according to the present invention can be suitably selected in accordance with the purpose of use of said ester and the form of agent. Examples of usable alcoholic compound include alkanol and alkandiol such as methanol, ethanol, propanol, butanol, isopropyl alcohol, tert-butyl alcohol, lauryl alcohol, myristyl alcohol, butanediol, ethylene glycol and propylene glycol; alkanpolyol such as glycerol; polyglycol such as polyethylene glycol and polypropylene glycol; sugar alcohol such as sorbitol, mannitol and dulcitol; sugar such as cane sugar, fruit sugar and glucose; sorbitan and cholesterol. Of these are preferable monohydric alcohols, polyhydric alcohols, polyethylene glycol and polypropylene glycol.

The ester of the N-acylamino acid containing acyl groups having odd-numbered carbon atoms in the Cosmetics II according to the present invention can be prepared usually from the above-mentioned N-acylamino acid containing acyl groups having odd-numbered carbon atoms and the alcoholic compound by means of esterification reaction, or by reacting an amino acid ester and a higher fatty acid chloride, said amino acid ester being prepared, in advance, from the amino acid and the aforesaid alcoholic compound.

The N-acylamino acid ester as mentioned above may be used alone or in combination with at least one other.

The amount of the ester of the N-acylamino acid containing acyl groups having odd-numbered carbon atoms to be added in the Cosmetics II according to the present invention can be suitably determined in accordance with the purpose of use, the mode of formulation, etc., and is usually selected flammatory agents, keratolytics, disinfectants and antiseptics.

The cosmetics of the present invention are not specifically limited in the form, but can be prepared into a variety of forms such as liquid, powder, cream and paste. Moreover, the cosmetics can be made into a variety of marketable products such as hair growth agent, hair grooming agent, lotion, hair rinse and skin cream, and are particularly useful for hair growth agent and hair grooming agent.

In the following, some description will be given of the N-acylamino acid composition of the present invention.

The N-acylamino acid composition of the present invention comprises at least one member selected from the group consisting of a N-acylamino acid containing an acyl group having odd-numbered carbon atoms, a salt thereof and an ester thereof.

As the amino acid to be used for the production of the above-mentioned N-acylamino acid containing an acyl group having odd-numbered carbon atoms, a salt thereof, and an ester thereof, amino acids such as an amino acid of natural origin, a non-proteinic amino acid and an amino acid produced by chemical synthesis can be used and are exemplified by an α-amino acid, β-amino acid, γ-amino acid, δ-amino acid, aliphatic amino acid, aromatic amino acid, heterocyclic amino acid, neutral amino acid, basic amino acid and acidic amino acid. There are also usable amino acids having optical isomerism such as L-, D- and racemic isomers. Specific in the range of 0.01 to 20% by weight based on the whole weight of the compositon. The amount thereof to be blended therein, when less than 0.01% by weight, sometimes leads to failure to exert the effect of the present invention. On the contrary, the amount thereof, when more than 20% by weight, is not favorable from the viewpoint of economical efficiency since the working effect approaches the uppermost limit.

The Cosmetics I and II according to the present invention can be prepared from the aforestated specific N-acylamino acid, the salt thereof or the ester thereof in the presence of a solvent, when necessary. Any solvent can be used, provided that the aforesaid compound is soluble therein, and an alcoholic solvent is preferably usable from the aspect of affinity for human skin. Usable solvents are specifically exemplified by methanol, ethanol, propyl alcohol, isopropyl alcohol, glycerol, propylene glycol, polyethylene glycol and n-paraffin.

The Cosmetics according to the present invention may be blended, at need, with another component to the extent that such blending does not impair the object of the present invention, in addition to the principal component such as the specific N-acylamino acid, the salt thereof or the ester thereof. Such another component is suitably selected in accordance with the purpose of use, type and form of the cosmetics, and is exemplified by base materials such as distilled water, alcohols, polyhydric alcohols, surfactants, fats and oils and polysaccharides, colorants, perfumes, vitamins, amino acids, hormones, vasodilators, anti- examples of the above-mentioned amino acids include alanine, valine, leucine, isoleucine, methionine, tryptophan, phenylalanine, glycine, serine, threonine, cysteine, tyrosine, asparagine, glutamine, lysine, arginine, aspartic acid, β-alanine, hydroxy-lysine, ornithine, citrulline, 5-aminolevulinic acid and γ-aminobutyric acid.

As the specific N-acylamino acid to be used in the composition according to the present invention, for example, the compound represented by the general formula (I) is used. The saturated or unsaturated straight chain aliphatic hydrocarbon group having even-numbered carbon atoms which is represented by R is preferably the group represented by $CH_3(CH_2)_m-$, wherein m is an odd integer from 5 to 17.

As the acyl group having odd-numbered carbon atoms in the specific N-acylamino acid, there is usable an acyl group having carbon atoms in an odd number in the range of 7 to 19, preferably 11 to 19, more preferably 13 to 17. In the case where the number of carbon atoms departs from the aforesaid range, the effect of the present invention is sometimes not sufficiently achieved.

Examples of the salt of the specific N-acylamino acid to be used in the compositon of the present invention include the examples same as those described of the salt of N-acylamino acid in the above-mentioned Cosmetics I.

With regard to the ester of the specific N-acylamino acid to be used in the compositon of the present invenion, the alcoholic compound to be used for forming the ester and the process for producing the ester are each same as the description given in the foregoing Cosmetics II.

Any of the specific N-acylamino acid, the salt thereof and the ester thereof may be used alone or in combination with at least one other. The amount thereof to be blended in the composition can be suitably determined in accordance with the purpose of use, the mode of formulation, etc., and is usually selected in the range of 0.01 to 90% by weight based on the whole weight of the composition. The amount thereof to be blended therein, when less than 0.01% by weight, sometimes leads to failure to sufficiently exert the effect of the present invention. On the contrary, the amount threreof, when more than 90% by weight, sometimes brings about poor handleability depending upon the purpose of use, since the resultant composition is made powdery, dependent on the formulation. The blending amount of the specific N-acylamino acid is preferably in the range of 0.01 to 90% by weight when used in toilet soap, preferably in the range of 0.01 to 20% by weight when used in lotion, and preferably in the range of 0.01 to 50% by weight when used in shampoo.

The composition according to the present invention may be blended, at need, with another component to the extent that such blending does not impair the object of the present invention, in addition to the principal component such as the specific N-acylamino acid, the salt thereof or the ester threof. Such another component is suitably selected in accordance with the purpose of use, type and form of the composiiton, and is exemplified by base materials such as distilled water, alcohols, polyhydric alcohols, fatts and oils, polysaccharides and surfactants, lather boosters, thickening agents, perfumes, pigments, dyes, water-solubility improvers, vitamins, amino acids, hormones, vasodilators, anti-flammatory agents, keratolytics and disinfectants.

The composition of the present invention is not specifically limited in its mode of use, but can be prepared into a variety of forms such as liquid, powder, cream, mousse and paste. Moreover, the composition can be made into marketable products such as detergent, dispersant, emulsifying agent, antimicrobial agent, antiseptics, ultraviolet absorbers, etc. and more specifically, cosmetics for face washing, shampoo, synthetic soap, toilet soap, body lotion, skin cream, rinse, aqueous cosmetics, antiperspirant, bathing agent and the like.

In the last place, some description will be given of the N-acylamino acid, the salt thereof and the ester thereof according to the present invention.

The specific N-acylamino acid is that in which an acyl group having carbon atoms in an odd number in the range of 13 to 17 has been introduced in at least one amino group of an amino acid. As the aforesaid amino acid, there is usable the amino acid same as that described in the above-mentioned cosmetics.

The specific N-acylamino acid according to the present invention is represented, for example, by the general formula (IV)

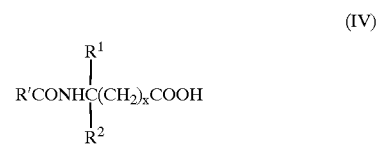

wherein R' is a straight chain aliphatic hydrocarbon group haivng carbons atom in an even number in the ragne of 12 to 16 which may have substituent groups and $R^1$, $R^2$ and x are each as previously defined in the general formula (I).

The hydrocarbon group represented by RI in the general formula (IV) may be saturated or unsaturated, and is exemplified, for example, by $CH_3(CH_2)_p$—, wherein p is an odd integer from 11 to 15.

In the case where the N-acylamino acid represented by the general formula (IV) is used for cosmetics such as a hair growth agent or hair grooming agent, the compound represented by the general formula (V) is preferably usable.

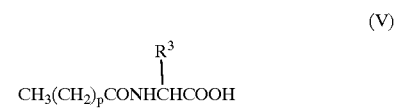

wherein $R^3$ is —$(CH_2)_y$COOH in which y is as previously defined in the general formula (I), and p is as just defined. In this case, a compound in which y is 1 or 2 is preferably used.

It is preferable that the above-mentioned specific N-acylamino acid be derived from an acidic amino acid from the aspect of amino acid, particularity preferably from N-acylasparatic acid. Preferably, the specific N-acylamino acid is derived from N-tridecanoylamine, N-pentadecanoylamine or N-heptadecanoylamine from the aspect of acyl group.

On the other hand, the N-acylamino acid salt of the present invention, which is a salt of the aforesaid specific N-acylamino acid, is exemplified by the N-acylamino acid salts same as those described in the Cosmetics I.

The N-acylamino acid ester of the present invention, which is an esterified compound formed from the aforesaid specific N-acylamino acid and an alcoholic compound, has already been described in the section of the Cosmetics II with respect to the alcoholic compound as well as the process for the production of the ester.

The specific N-acylamino acid, the salt thereof and the ester thereof according to the present invention have each excellent surface active action, disinfecting action, metal corrosion inhibiting action, hair growth promoting action, humectant action, subcutaneous blood flow rate increasing action and the like, and thus are usable for hair growth agent, hair grooming agent, detergent, dispersant, emulsifying agent, antimicrobial agent, antiseptics, ultraviolet absorber, etc. and more specifically, for hair grooming agent, hair liquid, hair cream, cosmetics for face washing, shampoo, synthetic soap, toilet soap, body lotion, skin cream, rinse, aqueous cosmetics, antiperspirant, bathing agent and so forth. Furthermore, the specific N-acylamio acid, the salt thereof and the ester thereof according to the present invention can expand the use to physiologically active fields such as anticancer drug and antiviral drug.

The N-acylamino acid containing acyl groups having odd-numbered carbon atoms according to the present invention can be synthesized, for example, by the condensation reaction between a higher fatty acid chloride having odd-numbered carbon atoms and an amino acid on the basis of the so called Schotten Baumann reaction or the method described in "Biochemistry" vol 35, No. 2, pp 67 to 74, 1963, Research on Polyamino Acid (I). The higher fatty acid having odd-numbered carbon atoms can be synthesized by a conventional method, specifically by the oxo process from an α-olefin having even-numbered carbon atoms and by the process using microorganism as described in Japanese Patent Application Laid-Open No. 253866/1994.

By the use of the N-acylamino acid containing an acyl group having odd-numbered carbon atoms, the salts thereof and the esters thereof according to the present invention, it is made possible to obtain the cosmetics which have excellent hair growth promoting effect, humectant action, subcutaneous blood flow rate increasing action and the like and thus are well suited for hair growth, skin care, etc.; the N-acylamino acid composiiton which has excellent surface active action, disinfecting action, metal corrosion inhibiting action, etc. and thus is useful as a detergent, dispersant, emulsifying agent, antimicrobial drug, antiseptics, ultraviolet absorber and the like.

In the following, the present invention will be described in more detail with reference to comparative examples and working examples, which however shall not limit the present invention thereto.

EXAMPLE 1
Synthesis of N-tridecanoyl-L-aspartic acid
(1) Synthesis of tridecanoyl chloride In a one L (liter) two-necked flask were placed 158.7 g (0.74 mol) of tridecanoic acid and 200 milliliter (mL) of cyclohexane, and the flask was equipped with a 100 mL dropping funnel containing 83.3 g (0.7 mol) of thionyl chloride and a reflux tube. Then, the tridecanoic acid was completely dissolved under heating and stirring of the flask in an oil bath at 80° C. Thereafter the thionyl chloride was added dropwise over a period of 2 hours, and further the oil bath was maintained at 80° C. for one hour. From the resultant reaction solution were removed the cyclohexane and the thionyl chloride under reduced pressure by means of an aspirator. The resultant reaction mixture was subjected to vacuum distillation. Thus 166.0 g (0.71 mol) of tridecanoyl chloride was obtained in a yield of 95.9% based on the fed tridecanoic acid.

(2) Synthesis-of N-tridecanoyl-L-aspartic acid

In a one L three-necked flask were placed 15.8 g (0.12 mol) of L-aspartic acid and an aqueous solution of 9.6 g (0.24 mol) of sodium hydroxide in 150 mL of water under stirring. After the L-aspartic acid was dissolved, 120 mL of acetone was added to the mixture in the flask. Then, to the resultant reaction liquid which had been cooled to 0° C. were added dropwise over a period of 30 minutes, 23.3 g (0.1 mol) of tridecanoyl chloride and an aqueous solution of 4 g of sodium hydroxide in 30 mL of water simultaneously therewith, while maintaining the reaction temperature at 0 to 5° C. and pH at 11 to 12. Thereafter, by gradually raising the temperature of the reaction liquid to room temperature (25° C.) under stirring over a period of 2 hours, a solution of disodium tridecanyol-L-aspartate was obtained. To the resultant solution was added 65 mL of 5N hydrochloric acid to lower the pH of the solution to 1. The crystal thus percipitated was separated from the solution by means of vacuum filtration, washed with water and dried under reduced pressure. The resultant crystal was washed with 500 mL of hexane, dried and recrystallized from a mixed solvent of ethanol/water (3:7 v/v). As a result 14.4 g (0.044 mol) of N-tridecanoyl-L-aspartic acid was obtained in a yield of 36.8% based on the fed tridecanoyl chloride. The physical properties of the objective N-tridecanoyl-L-aspartic acid were as follows.

$^1$H-NMR (CD$_3$OD); δ (ppm)

0.89 (t, 3H)

1.29 (s, 22H)

1.55 to 1.65 (m, 2H)

2.23 (t, 2H)

2.72 to 2.92 (m, 1H)

4.74 (dd, 1H)

IR (cm$^{-1}$);

3353, 3310, 2926, 1725, 1296, 1196, 928

Elemental analysis (C$_{17}$H$_3$ NO$_5$)

Found: C62.15%, H9.54%, N4.22%

Calculated : C61.98%, H9.48%, N4.25%

Melting point: 117.5 to 119.7° C

EXAMPLE 2
Synthesis of N-tridecanoyl-L-aspartic acid monosodium salt

In a 500 mL two-necked flask were placed 10.0 g (0.03 mol) of N-tridecanoyl-L-aspartic acid which had been obtained in Example 1, then 300 mL of water followed by stirring and further an aqueous solution of 1.2 g (0.03 mol) of sodium hydroxide in 50 mL of water, and the flask was heated to 50° C. in a hot water bath to produce an aqueous solution of N-tridecanoyl-L-aspartic acid monosodium salt. The resultant aqueous solution was allowed to cool to room temperature to precipitate crystal, which was filtered and dried under reduced pressure. Thus, 8.53 g (0.024 mol) of N-tridecanoyl-L-aspartic acid monosodium salt was obtained in a yield of 80.0% based on the fed N-tridecanoyl-L-aspartic acid.

EXAMPLE 3
Synthesis of N-tridecanoyl-L-aspartic acid disodium salt

In a 300 mL flask were placed 2.1 g (6.0 mmol) of N-tridecanoyl-L-aspartic acid monosodium salt which had been obtained in Example 2, then 100 mL of water followed by stirring and further an aqueous solution of 0.24 g (6.0 mmol) of sodium hydroxide in 20 mL of water to produce an aqueous solution of N-tridecanoyl-L-aspartic acid disodium salt. The resultant aqueous solution was lyophilized. Thus, 2.12 g (5.7 mmol) of N-tridecanoyl-L-aspartic acid disodium salt was obtained in a yield of 95.0% based on the fed N-tridecanoyl-L-aspartic acid monosodium salt.

EXAMPLE 4
Synthesis of N-pentadecanoyl-L-aspartic acid
(1) Synthesis of pentadecanoyl chloride In a one L (liter) two-necked flask were placed 160.0 g (0.66 mol) of pentadecanoic acid and 200 milliliter (mL) of cyclohexane, and the flask was equipped with a 100 mL dropping funnel containing 83.3 g (0.7 mol) of thionyl chloride and a reflux tube. Then, the pentadecanoic acid was completely dissolved under heating and stirring of the flask in an oil bath at 80° C. Thereafter the thionyl chloride was added dropwise over a period of 2 hours, and further the oil bath was maintained at 80° C. for one hour. From the resultant reaction mixture were removed the cyclohexane and the thionyl chloride under reduced pressure by means of an aspirator. The resultant crude reaction product was subjected to vacuum distillation. Thus 110.0 g (0.42 mol) of pentadecanoyl chloride was obtained in a yield of 63.9% based on the fed pentadecanoic acid.

(2) Synthesis of N-pentadecanoyl-L-aspartic acid

In a one L three-necked flask were placed 31.9 g (0.24 mol) of L-aspartic acid and an aqueous solution of 19.2 g (0.48 mol) of sodium hydroxide in 150 mL of water under stirring. After the L-aspartic acid was dissolved, 120 mL of acetone was added to the mixture in the flask. Then, to the resultant reaction liquid which had been cooled to 0° C. were added dropwise over a period of 30 minutes, 52.2 g (0.2 mol) of pentadecanoyl chloride and an aqueous solution of 0.2N sodium hydroxide in 30 mL of water simultaneously therewith, while maintaining the reaction temperature at 0 to 5° C. and pH at 11 to 12. Thereafter, by gradually raising the temperature of the reaction liquid to room temperature (25° C) under stirring over a period of 2 hours, a solution of disodium pentadecanoyl-L-aspartate was obtained. To the resultant solution was added 140 mL of 5N hydrochloric acid to lower the pH of the solution to 1. The crystal thus precipitated was separated from the solution by means of vacuum filtration, washed with water and dried under reduced pressure. The resultant crystal was washed with 500 mL of hexane, dried and recrystallized from a mixed solvent of ethanol/water (1:1 v/v). As a result 39.8 g (0.11 mol) of N-pentadecanoyl-L-aspartic acid was obtained in a yield of 55.6% based on the fed pentadecanoyl chloride. The physical properties of the objective N-pentadecanoyl-L-aspartic acid were as follows.

$^1$H-NMR (CD$_3$OD); δ (ppm)

0.89 (t, 3H)

1.28 (s, 26H)

1.55 to 1.65 (m, 2H)

2.23 (t, 2H)

2.72 to 2.92 (m, 1H)

4.74 (dd, 1H)

IR (cm$^{-1}$);

3353, 3310, 2926, 1725, 1296, 1196, 928

Elemental analysis (C$_{19}$H$_{35}$NO$_5$)

Found: C63.10%, H9.53%, N4.08%

Calculated: C63.84%, H9.87%, N3.92%

Melting point: 122.8 to 124.0° C.

EXAMPLE 5

Synthesis of N-pentadecanoyl-L-aspartic acid monosodium salt

In a 500 mL two-necked flask were placed 20.0 g (0.056 mol) of N-pentadecanoyl-L-aspartic acid which had been obtained in Example 4, then 300 mL of water followed by stirring and further an aqueous solution of 2.3 g (0.057 mol) of sodium hydroxide in 50 mL of water, and the flask was heated to 50° C. in a hot water bath to produce an aqueous solution of N-pentadecanoyl-L-aspartic acid monosodium salt. The resultant aqueous solution was allowed to cool to room temperature to precipitate crystal, which was filtered and dried under reduced pressure. Thus, 19.85 g (0.052 mol) of N-pentadecanoyl-L-aspartic acid monosodium salt was obtained in a yield of 93.5% based on the fed N-pentadecanoyl-L-aspartic acid.

EXAMPLE 6

Synthesis of N-pentadecanoyl-L-aspartic acid disodium salt

In a 300 mL flask were placed 2.1 g (5.5 mmol) of N-pentadecanoyl-L-aspartic acid monosodium salt which had been obtained in Example 5, then 100 mL of water followed by stirring and further an aqueous solution of 0.22 g (5.5 mmol) of sodium hydroxide in 20 mL of water to produce an aqueous solution of N-pentadecanoyl-L-aspartic acid disodium salt. The resultant aqueous solution was lyophilized. Thus, 2.19 g (5.5 mmol) of N-pentadecanoyl-L-aspartic acid disodium salt was obtained in a yield of 98.6% based on the fed N-pentadecanoyl-L-asparatic acid monosodium salt.

EXAMPLE 7

Synthesis of N-heptadecanoyl-L-aspartic acid (1) Synthesis of heptadecanoyl chloride In a one L (liter) two-necked flask were placed 102.1 g (0.38 mol) of heptadecanoic acid and 200 milliliter (mL) of cyclohexane, and the flask was equipped with a 100 mL dropping funnel containing 67.3 g (0.57 mol) of thionyl chloride and a reflux tube. Then, the heptadecanoic acid was completely dissolved under heating and stirring of the flask in an oil bath at 80° C. Thereafter the thionyl chloride was added dropwise over a period of 2 hours, and further the oil bath was maintained at 80° C. for one hour. From the resultant reaction mixture were removed the cyclohexane and the thionyl chloride under reduced pressure by means of an aspirator. The resultant reaction mixture was subjected to vacuum distillation. Thus 88.5 g (0.31 mol) of heptadecanoyl chloride was obtained in a yield of 81.2% based on the fed heptadecanoic acid.

(2) Synthesis of N-heptadecanoyl-L-aspartic acid

In a one L three-necked flask were placed 16.0 g (0.12 mol) of L-aspartic acid and an aqueous solution of 9.6 g (0.24 mol) of sodium hydroxide in 150 mL of water under stirring. After the L-aspartic acid was dissolved, 120 mL of acetone was added to the mixture in the flask. Then, to the resultant reaction liquid which had been cooled to 0° C. were added dropwise over a period of 30 minutes, 29.0 g (0.1 mol) of heptadecanoyl chloride and an aqueous solution of 4 g sodium hydroxide in 30 mL of water, while maintaining the reaction temperature at 0 to 5° C. and pH at 11 to 12. Thereafter, by gradually raising the temperature of the reaction liquid to room temperature (25° C.) under stirring over a period of 2 hours, a solution of disodium heptadecanoyl-L-aspartate was obtained. To the resultant solution was added 65 mL of 5N hydrochloric acid to lower the pH of the solution to 1. The crystal thus precipitated was separated from the solution by means of vacuum filtration, washed with water and dried under reduced pressure. The resultant crystal was washed with 500 mL of hexane, dried and recrystallized from a mixed solvent of ethanol/water (8:1). As a result 21.0 g (0.054 mol) of N-heptadecanoyl-L-aspartic acid was obtained in a yield of 54.3% based on the fed heptadecanoyl chloride. The physical properties of the objective N-heptadecanoyl-L-aspartic acid were as follows.

$^1$H-NMR (CD$_3$OD); δ (ppm)

0.89 (t, 3H)

1.28 (s, 30H)

1.55 to 1.65 (m, 2H)

2.23 (t, 2H)

2.72 to 2.92 (m, 1H)

4.74 (dd, 1H)

IR (cm$^{-1}$);

3353, 3310, 2926, 1725, 1296, 1196, 928

Elemental analysis (C$_{21}$H$_{39}$NO$_5$)

Found: C65.34%, H10.07*, N3.85%

Calculated: C65.42%, H10.20%, N3.63%

Melting point : 126.4 to 128.5° C.

EXAMPLE 8

Synthesis of N-pentadecanoyl-L-aspartic acid methyl ester and N-pentadecanoyl-L-aspartic acid dimethyl ester In a 200 mL two-necked flask were placed 1.04 g (2.91 mmol) of N-pentadecanoyl-L-aspartic acid as obtained in Example 4, 20 mL of methanol to dissolve said acid and 0.5 mL of a 14% solution of boron trifluoride in methanol. The flask, which was equipped with a reflux tube, was placed in a hot water bath at 50° C. to proceed with esterification at 50° C. for 2 hours. The resultant reaction mixture was allowed to cool to room temperature, then incorporated with 25 mL of 50 g/L aqueous solution of sodium chloride, and extracted with 40 mL of diethyl ether. The resultant ether layer was washed with 40 mL of water and dehydrated with sodium sulfate anhydride. The resultant extract, from which the solvent was removed under reduced pressure, was dried overnight to afford crystalline reaction product. By the use of a silica-gel column chromatography of 40 mm in diameter and 110 mm in length, a first fraction was obtained by the fractionation of said reaction product with 600 mL of chloroform, and a second fraction was obtained in the same manner with 200 mL of a mixed solvent of chloroform:methanol (2:1200 v/v). Each of the fractions, from which the solvent was removed under reduced pressure, was dried to produce 0.29 g (0.76 mmol) of N-pentadecanoyl-L-aspartic acid dimethyl ester in a yield of 26% from the first fraction and 0.61 g (1.63 mmol) of N-pentadecanoyl-L-aspartic acid methyl ester in a yield of 56% from the second fraction.

EXAMPLES 9 TO 12 AND COMPARATIVE EXAMPLES 1 TO 6

The surface tension and foaming power were examined by the following mehtods for each of N-acylamino acid salts that had been synthesized in Examples 1 to 8 or mutatis mutandis according thereto. The results are given in Table 1, which include those of N-acylleucine monosodium salt, N-acylaspartic acid monosodium salt and N-acylaspartic acid disodium salt.

Surface tension test

Measurements were made of the surface tension of 0.3% by weight aqueous solution of N-acylamino acid salts at 40° C. except for N-acylaminoaspartic acid at 60° C. by means of ring method.

Foaming power test 20 mL of 0.1% by weight aqueous solution of a N-acylamino acid salt was placed in a 100 mL graduated cylinder with a ground-in stopper, which was stoppered and vigorously shaked vertically. Immediately thereafter the cylinder containing the solution was allowed to stand on a horizontal place. An evaluation was made of the foaming power of the solution in question at 40° C. from the reading of the foam volume using the graduations on the cylinder.

TABLE 1-1

|  | N-acylamino acid salt | Number of carbon atoms of acyl group | Surface tension (mN/m) | Foaming Power |
|---|---|---|---|---|
| Example 9 | N-pentadecanoylleucine monosodium salt | 15 | 33.4 | 98 |
| Comparative Example 1 | N-myristoylleucine monosodium salt | 14 | 36.9 | 95 |
| Comparative Example 1 | N-palmitoylleucine monosodium salt | 16 | 34.2 | 70 |

TABLE 1-2

|  | N-acylamino acid salt | Number of carbon atoms of acyl group | Surface tension (mN/m) |
|---|---|---|---|
| Example 10 | N-tridecanoylasparatic acid monosodium salt | 13 | 22.6 |
| Comparative Example 3 | N-lauroylasparatic acid monosodium salt | 12 | 24.0 |

TABLE 1-2-continued

|  | N-acylamino acid salt | Number of carbon atoms of acyl group | Surface tension (mN/m) |
|---|---|---|---|
| Comparative Example 4 | N-myristoylasparatic acid monosodium salt | 14 | 24.2 |

TABLE 1-3

|  | N-acylamino acid salt | Number of carbon atoms of acyl group | Surface tension (mN/m) | Foaming Power |
|---|---|---|---|---|
| Example 11 | N-tridecanoylasparatic acid disodium salt | 13 | 21.7 | 20 |
| Example 12 | N-pentadecanoyl-asparatic acid disodium salt | 15 | — | 26 |
| Comparative Example 5 | N-lauroylasparatic acid disodium salt | 12 | 24.7 | 16 |
| Comparative Example 6 | N-myristoylasparatic acid disodium salt | 14 | 21.9 | 12 |

EXAMPLES 13 TO 15 AND COMPARATIVE EXAMPLES 7 TO 9

A group of eight male mice aged 8 weeks of C3H series with a body weight of 18 to 24 g were each subjected to depilation at a back portion thereof in about 2×3.5 cm size. Then 1% by weight solution of any of the N-acylamino acid compounds in ethanol as shown in Table 2 as a sample to be tested was applied to the depilated back portion once a day in an amount of 0.1 mL over a period of 3 weeks to observe the fur growth state. An evaluation was made of the fur growth effect by taking a photograph of the back portion area of each mouse to be tested and obtaining the trichogenous factor, that is, the ratio of trichogenous portion area to the whole area to be test from the photograph thus taken by means of a planimeter. The results are given in Table 2 for each of N-acylaminoaspartic acid and N-acylaminoglutamic acid. According to the results, favorable fur growth effect was recognized in N-acylamino acids each containing an acyl group having odd-numbered carbon atoms. In addition, no influence by the coating of the samples to be tested was recognized throughout the testing period with regard to general symptom, dermal state and change in body weight. The acylamino acid compounds used in this test were those synthesized in Examples 1 to 8 or mutatis mutandis according thereto.

TABLE 2-1

|  | N-acylamino acid salt | Number of carbon atoms of acyl group | Trichogenous factor on 14th day (%) |
|---|---|---|---|
| Example 13 | N-pentadecanoyl-aspartic acid | 15 | 46.8 |
| Example 14 | N-tridecanoyl-aspartic acid | 13 | 34.1 |
| Comparative Example 7 | N-dodecanoyl-aspartic acid | 12 | 29.8 |
| Comparative Example 8 | ethanol | — | 21.6 |

TABLE 2-2

| N-acylamino acid salt | | Number of carbon atoms of acyl group | Trichogenous factor on 14th day (%) |
|---|---|---|---|
| Example 15 | N-tridecanoyl-glutamic acid | 13 | 27.3 |
| Comparative Example 9 | N-dodecanoyl-glutamic acid | 12 | 21.6 |
| Comparative Example 8 | ethanol | — | 21.6 |

In the following, a variety of cosmetics along with forms and chemical compositions are given as additional examples according to the present invention.

Example 16 Hair grooming agent

| | % by weight |
|---|---|
| Ethanol | 78.0 |
| N-pentadecanoylasparatic acid | 0.5 |
| Olive oil | 1.0 |
| α-Tocopherol | 0.5 |
| Perfume | 0.5 |
| Purified water | 19.5 |
| Antiseptics | proper amount |

Example 17 Hair grooming agent

| | % by weight |
|---|---|
| Ethanol | 60.0 |
| N-tridecanoylglutamic acid | 0.5 |
| Dipropylene glycol | 3.0 |
| Perfume | 0.5 |
| Purified water | 36.0 |
| Antiseptics | proper amount |

Example 18 Hair liquid

| | % by weight |
|---|---|
| Ethanol | 40.0 |
| N-pentadecanoylaspartic acid | 2.0 |
| Glycerol | 1.0 |
| Polyoxyethylene glycol monoether | 10.0 |
| Perfume | 0.5 |
| Purified water | 46.5 |
| Antiseptics | proper amount |

Example 19 Hair cream

| | % by weight |
|---|---|
| N-pentadecanoylasparatic acid | 10.0 |
| Liquid paraffin | 30.0 |
| Sorbitan monooleate | 2.0 |
| Perfume | 0.5 |
| Purified water | 57.5 |
| Antiseptics | proper amount |

EXAMPLES 20 TO 33 AND COMPARATIVE EXAMPLES 10 TO 12

A group of eight male mice aged 8 weeks of C3H series with a body weight of 18 to 24 g were each subjected to depilation at a back portion thereof in about 2×3.5 cm size. Then 1% by weight solution of any of the N-acylamino acid compounds in ethanol as shown in Table 3 as a sample to be tested was applied to the depilated back portion once a day in an amount of 0.1 mL over a period of 3 weeks to observe the fur growth state. An evaluation was made of the fur growth effect by visually observing the state of trichogenous promotion in the area to be tested in comparison with the back portion coated only with ethanol on the basis of the following evaluation criterion (see Remarks under Table 3). The results are given in Table 3. According to the results, favorable fur growth effect was recognized in the esters of N-acylamino acids each containing an acyl group having odd-numbered carbon atoms. In addition, no influence by the coating of the samples to be tested was recognized throughout the testing period with regard to general symptom, dermal state and change in body weight. The acylamino acid ester compounds used in this test were those synthesized in Example 8 or mutatis mutandis according therto.

TABLE 3

| | N-acylamino acid ester | Evaluation |
|---|---|---|
| Example 20 | N-pentadecanoylaspartic acid methyl ester | ⊙ |
| Example 21 | N-tridecanoylaspartic acid methyl ester | ○ |
| Example 22 | N-heptadecanoylaspartic acid methyl ester | ○ |
| Example 23 | N-pentadecanoylaspartic acid dimethyl ester | ⊙ |
| Example 24 | N-pentadecanoylaspartic acid ethyl ester | ⊙ |
| Example 25 | N-pentadecanoylaspartic acid isopropyl ester | ⊙ |
| Example 26 | N-pentadecanoylaspartic acid hexadecyl ester | ○ |
| Example 27 | N-pentadecanoylaspartic acid ethylene glycol ester | ○ |
| Example 28 | N-pentadecanoylaspartic acid polyethylene glycol (n = 6) ester | ○ |
| Example 29 | N-tridedecanoylglutamic acid methyl ester | ○ |
| Example 30 | N-pentadecanoylvaline methyl ester | ○ |
| Example 31 | N-pentadecanoylthreonine methyl ester | ○ |
| Example 32 | N-pentadecanoylphenylalamine ethyl ester | ○ |
| Example 33 | N-pentadecanoyllysine methyl ester | ○ |
| Comp.* Example 10 | N-dodecanoylaspartic acid methyl ester | x |
| Comp.* Example 11 | N-myristoylaspartic acid | x |
| Comp.* Example 12 | N-dodecanoylglutamic acid methyl ester | x |

*Comp. means "Comparative"
[Remarks]
⊙ Strong trichogenous promotion
○ intermediate trichogenous promotion
Δ slight trichogenous promotion
x trichogenous promotion unobserved In the following, a variety of cosmetics along with forms and chemical compositions are given as additional examples according to the present invention.

Example 34 Hair grooming agent

| | % by weight |
|---|---|
| Ethanol | 75.0 |
| N-pentadecanoylaspartic acid methyl ester | 4.0 |
| Olive oil | 1.0 |
| α-Tocopherol | 0.5 |
| Perfume | proper amount |
| Antiseptics | proper amount |
| Purified water | balance |

Example 35 Hair grooming agent

| | % by weight |
|---|---|
| Ethanol | 60.0 |
| N-tridecanoylglutamic acid methyl ester | 3.0 |
| Isopropyl myristate | 2.0 |
| Perfume | proper amount |
| Antiseptics | proper amount |
| Purified water | balance |

Example 36 Hair tonic

| | % by weight |
|---|---|
| Ethanol | 60.0 |
| N-pentadecanoylaspartic acid methyl ester | 1.0 |
| Tocopherol acetate | 0.5 |
| Glycerol | 3.0 |
| L-menthol | 0.1 |
| Perfume | proper amount |
| Antiseptics | proper amount |
| Purified water | balance |

Example 37 Hair rinse

| | % by weight |
|---|---|
| Cetyltrimethylammonium chloride | 2.0 |
| Polyoxyethylene cetyl ether | 1.0 |
| Cetyl alcohol | 2.0 |
| N-tridecanoyllysine methyl ester | 1.0 |
| Propylene glycol | 5.0 |
| Perfume | proper amount |
| Purified water | balance |

Example 38 Foundation

| | % by weight |
|---|---|
| Stearic acid | 2.0 |
| Liquid lanolin | 2.0 |
| Liquid paraffin | 3.0 |
| N-tridecanoylvaline methyl ester | 2.0 |
| Isopropyl myristate | 5.0 |
| Sorbitan monooleate | 2.0 |
| Titanium oxide | 8.0 |
| Talc | 4.0 |
| Bentonite | 0.5 |
| Iron oxide red | 0.5 |
| Perfume | proper amount |
| Antiseptics | proper amount |
| Purified water | balance |

Example 39 Lipstick

| | % by weight |
|---|---|
| Titanium oxide | 1.0 |
| Rose Bengal | 4.0 |
| Castor oil | 50.0 |
| Octyl dodecanol | 10.0 |
| N-tridecanoylleucine methyl ester | 5.0 |
| Beeswax | 5.0 |
| Carnauba wax | 5.0 |
| Solid paraffin | 20.0 |
| Perfume | proper amount |
| Antiseptics | proper amount |

Example 40 Lotion

| | % by weight |
|---|---|
| Ethanol | 15.0 |
| Polyethylene glycol | 3.0 |
| N-pentadecanoylthreonine methyl ester | 1.0 |
| Polyoxyethylene sorbitan monolaurate | 2.0 |
| Perfume | proper amount |
| Antiseptics | proper amount |
| Purified water | balance |

Example 41 Vanishing cream

| | % by weight |
|---|---|
| Stearic acid | 15.0 |
| Petrolatum | 2.0 |
| N-pentadecanoylasparatic acid dimethyl ester | 1.0 |
| Polyoxyethylene sorbitan monostearate | 2.0 |
| Sorbitan monostearate | 2.0 |
| Propylene glycol | 10.0 |
| Perfume | proper amount |
| Antiseptics | proper amount |
| Purified water | balance |

Example 42 Cosmetic soap

| | % by weight |
|---|---|
| Pentadecanoylasparatic acid monosodium salt | 83.0 |
| Cetanol | 8.0 |
| Purified water | 8.5 |
| Perfume | 0.5 |

Example 43 Cleansing foam

| | % by weight |
|---|---|
| Tridecanoylasparatic acid mono tri ethanolamine salt | 25.0 |
| Myristic acid | 10.0 |
| Cetanol | 2.0 |
| Glycerol | 10.0 |
| Potassium hydroxide | 3.0 |
| Polyethylene glycol | 10.0 |
| Perfume | 0.5 |
| Purified water | 39.5 |

Example 44 Shampoo

| | % by weight |
|---|---|
| Pentadecanoylasparatic acid mono tri ethanolamine salt | 15.0 |
| Lauryl acid dithanolamide | 5.0 |
| Propylene glycol | 2.0 |
| Perfume | 0.1 |
| Purified water | 77.9 |

Example 45 Shampoo

| | % by weight |
|---|---|
| Tridecanoylasparatic acid monosodium salt | 5.0 |
| Polyoxyethylene sorbitan fatty acid ester | 5.0 |
| Sodium lauryl sulfate | 5.0 |
| Glycerol | 2.0 |
| Purified water | 83.0 |

Example 46 Lotion

| | % by weight |
|---|---|
| Pentadecanoylasparatic acid monosodium salt | 2.0 |
| Glycerol | 5.0 |
| Propylene glycol | 5.0 |
| Polyethylene glycol | 2.0 |
| Ethanol | 8.0 |
| Perfume | 0.1 |
| Purified water | 77.9 |

Example 47 Emollient Lotion

| | % by weight |
|---|---|
| Tridecanoylasparatic acid monosodium salt | 2.0 |
| Tridecanoylleucine monosodium salt | 1.0 |
| Beeswax | 0.5 |
| Petrolatum | 2.0 |
| Squalane | 5.0 |
| Propylene glycol | 5.0 |
| Ethanol | 5.0 |
| 1% aqueous solution of CMC | 20.0 |
| Potassium hydroxide | 0.1 |
| Perfume | 0.1 |
| Purified water | 59.3 |

Example 48 Lipstick

| | % by weight |
|---|---|
| Solid paraffin | 10.0 |
| Titanium oxide | 1.0 |
| Lanolin | 5.0 |
| Beeswax | 2.0 |
| Camauba wax | 2.0 |
| Heptadecanoylasparatic acid | 2.0 |
| Octadecanol | 15.0 |

Example 48 Lipstick

| | % by weight |
|---|---|
| Castor oil | 57.9 |
| Pigment | 5.0 |
| Perfume | 0.1 |

Example 49 Foundation

| | % by weight |
|---|---|
| Titanium oxide | 15.0 |
| Kaolin | 20.0 |
| Talc | 10.0 |
| Iron oxide red | 2.0 |
| Tridecanoyllysine | 2.0 |
| Sericin | 10.0 |
| Carnauba wax | 2.0 |
| Liquid paraffin | 21.5 |
| Isopropyl myristate | 15.0 |
| Sorbitan monooleate | 2.0 |
| Perfume | 0.5 |

What is claimed is:

1. A cosmetic, comprising at least one N-acylamino acid or salt thereof,
    wherein a total number of carbon atoms in the acyl group of the N-acylamino acid or salt thereof is 13, 15 or 17,
    and wherein the N-acylamino acid or salt thereof is derived from an amino acid selected from the group consisting of valine, phenylalanine, threonine, lysine, aspartic acid, and glutamic acid.

2. The cosmetic according to claim 1, wherein the amino acid is an acidic amino acid.

3. The cosmetic according to claim 2, wherein the acidic amino acid is glutamic acid or aspartic acid.

4. A cosmetic, comprising at least one N-acylamino acid ester,
    wherein a total number of carbon atoms in the acyl group of the N-acylamino acid ester is 13, 15 or 17,
    and wherein the N-acylamino acid ester is derived from an amino acid selected from the group is derived from an amino acid selected from the group consisting of valine, phenylalanine, threonine, lysine, aspartic acid, and glutamic acid.

5. The cosmetic according to claim 4, wherein the amino acid is an acidic amino acid.

6. The cosmetic according to claim 5, wherein the acidic amino acid is glutamic acid or aspartic acid.

7. The cosmetic according to claim 4, wherein the N-acylamino acid ester is derived from at least one alcohol selected from the group consisting of monohydric aliphatic alcohol, polyhydric aliphatic alcohol, polyethylene glycol and polypropylene glycol.

8. A composition, comprising at least one selected from the group consisting of N-acylamino acid, N-acylamino acid salt, and an N-acylamino acid ester,
    wherein a total number of carbons in the acyl group of the N-acylamino acid, N-acylamino acid salt or N-acylamino acid ester is 13, 15 or 17,
    wherein the N-acylamino acid, N-acylamino acid salt or N-acylamino acid ester is derived from an amino acid selected from the group consisting of valine, phenylalanine, threonine, lysine, aspartic acid and glutamic acid.

9. The composition according to claim 8, comprising an N-acylamino acid ester, and wherein the total number of carbon atoms is an odd number in the range of 13 to 17.

10. A hair growth promoting agent, comprising at least one N-acylamino acid or salt thereof, wherein said N-acylamino acid or salt thereof is present in a hair-growth promoting amount, wherein a total number of carbon atoms in the acyl group of the N-acylamino acid or salt thereof is 13, 15 or 17, and wherein the N-acylamino acid or salt thereof is derived from an amino acid selected from the group consisting of valine, phenylalanine, threonine, lysine, aspartic acid, and glutamic acid.

11. A method of promoting hair growth, comprising applying to the skin or scalp of a patient in need thereof, a composition comprising a hair-growth promoting amount of at least one N-acylamino acid or salt thereof, wherein a total number of carbon atoms in the acyl group of the N-acylamino acid or salt thereof is 13, 15 or 17, and wherein the N-acylamino acid or salt thereof is derived from an amino acid selected from the group consisting of valine, phenylalanine, threonine, lysine, aspartic acid, and glutamic acid.

* * * * *